United States Patent [19]

Nash

[11] 4,175,194
[45] Nov. 20, 1979

[54] PIPERIDINYLDITHIOCARBONIC ACID DERIVATIVES

[76] Inventor: Lawrence H. Nash, Fort Lauderdale, Fla.

[21] Appl. No.: 911,879

[22] Filed: Jun. 2, 1978

Related U.S. Application Data

[63] Continuation-in-part of Ser. No. 888,744, Mar. 21, 1978.

[51] Int. Cl.$^2$ .......................................... C07D 295/18
[52] U.S. Cl. ...................................... 546/189; 424/267
[58] Field of Search ..................... 260/293.63; 546/189

[56] References Cited

U.S. PATENT DOCUMENTS

| | | | |
|---|---|---|---|
| 1,972,961 | 9/1934 | Tisdale et al. | 260/293.85 |
| 2,342,481 | 2/1944 | Muller | 260/293.85 |
| 2,368,515 | 1/1945 | Blake | 260/293.73 |
| 2,414,014 | 1/1947 | Cable | 260/293.85 |

FOREIGN PATENT DOCUMENTS

| | | | |
|---|---|---|---|
| 960006 | 10/1949 | France | 260/455 A |
| 1369306 | 7/1964 | France | 260/455 A |

*Primary Examiner*—John M. Ford
*Attorney, Agent, or Firm*—Lowe, King, Price & Becker

[57] ABSTRACT

Compounds of the formula:

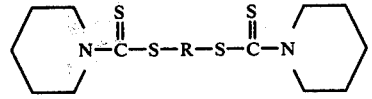

wherein R is selected from the group consisting of $S_x$, (wherein x is a whole number from 1 to 3), SO, $SO_2$, $S_2O_3$, $S_2O_4$, $S_2O_5$.

4 Claims, No Drawings

PIPERIDINYLDITHIOCARBONIC ACID DERIVATIVES

CROSS-REFERENCE TO RELATED APPLICATION

This application is a continuation-in-part of my co-pending U.S. application Ser. No. 888,744, filed Mar. 21, 1978.

BACKGROUND OF THE INVENTION

The present invention relates to novel piperidinyldithiocarbonic acid derivatives that are free of undesired degradation products which have been regarded as a potential source of environmental hazard to mammalian species, including man.

Dithiocarbamates and dithiocarbonates are well known in the art and have been used for diverse purposes. They are not widely accepted because of the impurities in the products which are deleterious to human, animals and plants. A major objection to the products of the prior art is that they are carcinogenic and a hazard to the environment. Therefore, there is a need to overcome the disadvantages of the prior art products and render them more useful for their intended usage.

The process of preparing dithiocarbamates and dithiocarbonates by prior art methods are dangerous and hazardous, resulting in the formation of side reaction products. The process creates a physical hazard and danger to the workers producing the dithiocarbamates and dithiocarbonates. Therefore, there is a need to overcome the hazardous formation of dithiocarbamates as well as the production of compounds that create environmental problems.

According to prior art methods, it was not possible to react a dithiocarbonate compound with compounds containing both sulfur and chlorine, e.g., thionyl chloride and sulfuryl chloride, because said compounds readily decomposed when placed in water. Although U.S. Pat. Nos. 1,798,588, 2,414,014, 3,116,328 and 3,193,580 teach the use of thionyl chloride and sulfuryl chloride as being capable of reacting with dithiocarbamates in water, the prior art recognizes that said thionyl chloride and sulfuryl chloride will decompose in water and thus cause the basic dithiocarbamic acid to precipitate. See, e.g.:

Comptes rendus hebdomadaires des seances de l'academie des sciences 62,461, (1866)
Gazzetta chimica italiano 24, 364, (1894)
Journal American Chemical Society 35, 543–546, (1913)
Svensk Kemisk Tidsckrift 13, 108, (1920)
Journal of the Chemical Society (London) 117, 1103 (1920)
Science 67, 19, (1928)
Monatshefte fur Chemie und verwandte Teile anderer Wissenschaften 93, 49, (1962)

OBJECT OF THE INVENTION

It is therefore a significant object of the present invention to provide a dithiocarbonate that is particularly effective for achieving complete control, complete extermination and removal of undesired pathogens after they have infested an area to be protected without contamination of the environment or damage to the plant to be protected.

Consistent with this object, it is a primary object to provide an improved dithiocarbonate that is free of side reaction products, alkali and metal, although alkalies may be used as reactants.

Another object of the invention is to provide dithiocarbonates when treated with sulphur and chlorine compounds (where sulphur and chlorine are in the same molecule) do not decompose in the reaction.

A still further object of the present invention is to provide an improved accelerator to improve the vulcanization of synthetic and natural rubber compounds, due to the purity of the accelerator.

A further object of the invention is the provision of a simple and efficient method for the preparation of the compounds of this invention.

Still another object of the invention is the provision of the novel compounds and compositions that exhibit a favorable rate of dissappearance from soil after application thereby avoiding residual action by remaining in the soil after the desired period for chemical control has passed.

Another object of the invention is to provide a pathological compound that is useful as a general fungicide on lawns, golf courses, parks, playgrounds, recreational areas, along highways, home gardens, farms, hot houses, potted plants, nurseries and wherever, with effects visible in a few days.

A further object of the invention is the provision of new dithiocarbonate compounds that do not have adverse effects on aquatic life nor on water so treated, when used for irrigation, human or animal purposes.

BRIEF SUMMARY OF THE INVENTION

Briefly, the invention relates to new compounds of the formula:

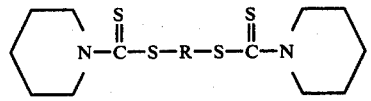

wherein R is selected from the group consisting of $S_x$, (wherein x is a whole number from 1 to 3), SO, $SO_2$, $S_2O_3$, $S_2O_4$, $S_2O_5$.

Compounds of this invention are formed by the reaction of two moles of piperidinyl dithiocarbonic acid, two moles of an alkali, e.g., an ammonium or alkali metal hydroxide, and a compound selected from the group consisting of: $SCl_2$, $S_2Cl_2$, $SOCl_2$, $SO_2Cl_2$, $S_2O_4Cl_2$, and $S_2O_5Cl_2$.

The alkali halide is then removed by filtration and suction, and the alcoholic solution taken to dryness by vacuum distillation. There are no side reaction-products or reactions taking place once the main reaction has taken place.

DETAILED DESCRIPTION OF THE INVENTION

Piperidinyldithiocarbonic acid used in this invention is prepared by adding a mole of piperidine to 500 ml. of cold water (5° C., approximately) in a reactor equipped with a stirring device, followed by one mole of $CS_2$ poured into the aqueous solution of piperidine. The reactor is then closed and the reactants vigorously agitated for a period of time sufficient for the reaction to take place which generally takes place within about 2 hours. Stirring for a longer period is not detrimental. The water-insoluble precipitate is then recovered by filtration and suction. The filter cake is then dissolved in chloroform, dried over sodium sulphate and filter clay. The drying can be accomplished by drawing warm air (about 70° to 75° C.) through the cake until dry or by washing with acetone or alcohol, refiltering and drying. Drying by drying towers, drying ovens and mechanical devices can be used providing the temperature of the crystalline piperidinyldithiocarbonic acid does not exceed 80 degrees centigrade.

This piperidinyldithiocarbonic acid is essentially chemically pure. Ultra-violet absorbency studies showed no particular peaks from 200 millimicrons up to 400 millimicrons, however, from 285 millimicrons into the visible range there is a high absorbency band.

Infra-red studies from 2.5 microns to 16 microns showed a number of absorption peaks, some of the major peaks were 3.4 and a reverse absorption peak at 3.6, a minor peak at 4.7, several minor peaks between 5.0 and 6.5, with major peaks at 7.2, 8.3, 9.0, 10.5, 11.8 and 13.0.

It should be noted that morpholine could replace piperidine but there are disadvantages associated with the use of morpholine, in the preparation of the dithiocarbonic acid as well as in the processing of the morpholinyldithiocarbonic acid.

The compounds of the present invention are formed by reacting two moles of piperidinyldithiocarbonic acid in 500 ml. of chloroform with one mole of a reactant selected from the group consisting of: (a) $SCl_2$, (b) $S_2Cl_2$, (c) $SOCl_2$, (d) $SO_2Cl_2$, (e) $S_2O_4Cl_2$, and (f) $S_2O_5Cl_2$, and two moles of potassium hydroxide. the reactants are vigorous stirred for one hour. The potassium chloride produced in the reaction is removed by filtration and suction and the product is taken to dryness under reduced heat and pressure. The compounds formed from these reactions, the potassium chloride being removed and the alcohol being recovered by vacuum distillation are: (a) Bis piperidinyldithiocarbonylsulphide, (b) Bis piperidinyldithiocarbonyldisulphide, (c) Bis piperidinyldithiocarbonylsulfoxide, (d) Bis piperidinyldithiocarbonylsulphur dioxide, (e) Bis piperidinyldithiocarbonylsulphurtetraoxide, and (f) Bis piperidinyldithiocarbonylsulphurpentaoxide.

The compounds of this invention can also be prepared by reacting 2 moles piperidinyldithiocarbonic acid and one mole of a reactant defined hereinabove, in 1000 ml. of methanol. The mixture is cooled to 5° C. (approximately). Two moles of crystalline potassium hydroxide is added to the mixture. The reactor is closed and the mixture vigorously stirred for a period of time to cause the reaction to go to completion which is about two hours. The same reaction products defined above, are produced.

COMPOSITIONS

In the formation of compositions for application as an anhydrous application, the compounds of this invention can be admixed with any of the well-known, free-flowing, particulate, dry, inert solid carriers which may be organic or inorganic, dry, inert solid carriers which may be organic or inorganic, including, e.g., sawdust, wood-by-products, lignin and lignin-cellulose, ligninsulfonic acid, cork, urea-formaldehyde, resins, silicas, carbonates, calcite, dolomite, silicates, tricalcium phosphate, boric acid, etc. In addition, the compositions may optionally contain a conventional wetting agent, which renders the product wettable and dispersable, thereby facilitating the application thereof in the field. The wetting agent can be anionic, non-anionic or cationic. Particularly useful wetting agents include those disclosed in Bulletin E-607 of the Bureau of Entology and Plant Quarantine of the United States Department of Agriculture or those disclosed in U.S. Pat. Nos. 2,426,417; 2,655,447; 2,412,510 and 2,139,276. A preferred surfactant is sodium lauryl sulfonate.

In addition, the compositions may optionally contain from about 0.5 to about 1.0 weight percent of a wetting agent, which renders the products wettable and dispersible, thereby facilitating the application thereof to plants in the field.

The ingredients may be simply mixed together thoroughly with agitation, in some cases the mixture may be passed through a high speed grinder to make the product free flowing.

Some of the products prepared with an anhydrous diluent are water soluble and are mixed with the anhydrous diluent only as an extender of the active ingredient. Such anhydrous diluents should also be water-soluble, such as diatomaceous earths.

EXAMPLE

Separate batches of each compound of this invention are formed by placing two moles of piperidinyldithiocarbonic acid dissolved in 500 ml. of chloroform with one moles of each reactant $SCl_2$, $S_2Cl_2$, $SOCl_2$, $SO_2Cl_2$, $S_2O_4Cl_2$, and $S_2O_5Cl_2$. The ingredients are vigorously agitated as two moles of potassium hydroxide are slowly added over a period of fifteen minutes to each batch of reactants. Salt formation is apparent when the potassium hydroxide is first introduced. Stirring is continued for one hour. The potassium chloride formed is removed by filtration and suction and the product taken to dryness under reduced heat and pressure. Since the chloroform is recovered at 61° C., there is not much heat consumed. The compounds formed are:

(a) Bis piperidinyldithiocarbonylsulphide.
(b) Bis piperidinyldithiocarbonyl disulphide.
(c) Bis piperidinyldithiocarbonyl sulfoxide.
(d) Bis piperidinyldithiocarbonylsulphurdioxide.
(e) Bis piperidinyldithiocarbonylsulphurtetraoxide.
(f) Bis piperidinyldithiocarbonylsulphurpentaoxide.

It should be noted that where potassium hydroxide is referred to in this invention, sodium hydroxide, lithium hydroxide and ammonium hydroxide can be used, however, potassium hydroxide is preferred.

Where ammonium sulphate is referred to in this invention, potassium sulphate or a mixture of ammonium sulphate and potassium sulphate may be used.

Where alcohols are used in this invention, they may be chosen from the alcohols disclosed in my U.S. Pat. No. 2,900,293.

What is claimed is:

1. The compound, Bis piperidinyldithiocarbonylsulfoxide.

2. The compound, Bis piperidinyldithiocarbonylsulfur dioxide.

3. The compound, Bis piperidinyldithiocarbonylsulfurtetraoxide.

4. The compound, Bis piperidinyldithiocarbonylsulfurpentaoxide.

* * * * *